United States Patent [19]

Whitbourne et al.

[11] 3,992,154

[45] Nov. 16, 1976

[54] ETHYLENE OXIDE STERILIZATION INDICATOR

[75] Inventors: James E. Whitbourne; Carolyn A. Eastman, both of Rochester, N.Y.

[73] Assignee: Sybron Corporation, Rochester, N.Y.

[22] Filed: Dec. 22, 1975

[21] Appl. No.: 643,189

[52] U.S. Cl. .............................. 23/253 TP; 252/408
[51] Int. Cl.[2] ........................................ G01N 31/22
[58] Field of Search ................. 23/253 TP, 232 R; 73/356; 116/114 AM; 252/408; 21/58

[56] References Cited
UNITED STATES PATENTS

| | | | |
|---|---|---|---|
| 2,798,855 | 7/1957 | Hainsworth | 252/408 |
| 3,232,710 | 2/1966 | Rieckmann et al. | 23/253 TP |
| 3,344,670 | 10/1967 | Olssen et al. | 23/230 R X |
| 3,585,112 | 6/1971 | Ernst | 195/103.5 R |
| 3,627,469 | 12/1971 | Cheng | 23/232 R |

*Primary Examiner*—Robert M. Reese
*Attorney, Agent, or Firm*—Theodore B. Roessel; Papan Devnani

[57] ABSTRACT

A monitoring device for use in ethylene oxide sterilizing systems consists of an envelope containing an indicator coated with a dye, which besides showing a color change on completion of sterilizing cycle also indicates the completion of the subsequent aeration cycle.

14 Claims, No Drawings

ETHYLENE OXIDE STERILIZATION INDICATOR

BACKGROUND OF THE INVENTION

This invention relates to a method of determining completeness of sterilization and aeration cycle in an ethylene oxide sterilizing process by the use of an indicator. Ethylene oxide sterilizing systems are well known in the art and are widely used in the hospitals and laboratories for destruction of microorganisms. Briefly in ethylene oxide sterilization, goods to be sterilized such as surgical instruments, rubber, and plastic devices, etc., are placed inside the sterilizing chamber and exposed for a period to ethylene oxide under controlled humidity and temperature conditions. The period cycles are usually timed to last 1 ½ hours to 4 hours depending upon the nature of articles being sterilized. After sterilization goods are placed in an aerator to dispel ethylene oxide. The validity of such sterilizing cycle is often determined by chemical indicators in hospital practice. Indicators used presently show the presence of ethylene oxide by a color change. A compound proposed for use as an exposure indicator for ethylene oxide sterilization has been described in the literature. Brewer and Arnsberger in Journal of Pharmaceutical Sciences, Vol. 55, No. 1, January 1966 pages 57–59, disclose that 4(4'-nitrobenzyl) pyridine reacts with ethylene oxide to form a dye which is blue in alkaline medium. Although this indicator has a high degree of specificity to ethylene oxide, the fact that it is too highly sensitive to this alkylating agent limits its utility to that of an exposure indicator, indicating merely that the material being treated has been exposed to ethylene oxide. In order to determine whether the extent of exposure to the alkylating agent has been sufficient to render sterility to the material being treated, it is necessary to rely upon the use of positive spore controls and then assay the effectiveness of kill, a procedure which has the disadvantage of being rather inconvenient and time consuming. Furthermore, the color change exhibited by this exposure indicator is inhibited by the presence of carbon dioxide, the principal inert diluent gas commonly employed with ethylene oxide. Attempts have been made to correct this problem. In U.S. Pat. No. 3,627,469 substituted pyridines quinolines or isoquinolines are suggested as indicators. However, their use is limited to sterilization process. They cannot be used to monitor aeration process.

Indicators monitoring dissipation of ethylene oxide are available and one such device is disclosed in U.S. Pat. No. 3,738,811, this device is not a true telltale indicator. The method according to this patent calls for frequent rupturing of an ampule and the moment of rupturing is merely a guess work. An accurate indication of aerating cycle is essential. Some intricate surgical instruments and medical devices if not completely aerated may still contain ethylene oxide and if used may be hazardous to patients and trigger malpractice suits against hospitals.

We have found that the problems associated with the use of 4-(4'nitrobenzyl) pyridine can be obviated by desensitizing it with additives. The proposed telltale indicator as described in this invention changes its color from white to violet during a sterilizing cycle and the same indicator remaining with the sterilized goods in the aerator indicates the completion of that cycle by a change of color from violet to gray green. No indicators are known in the prior art which show the completion of total ethylene oxide cycle, namely exposure to ethylene oxide as well as aeration, by a color change. This invention eliminates the need of two separate indicators.

BRIEF SUMMARY OF THE INVENTION

It is an object of this invention to provide a telltale indicator which monitors both the sterilization as well as the aeration cycle by a color change.

It is another object of this invention to provide a method of monitoring a sterilization and aeration process.

It is yet another object of this invention to provide a composition which undergoes a color change in the presence of ethylene oxide gas.

It is still another object of the invention to provide an indicator which shows completion of ethylene oxide sterilization cycle even in the presence of freon, carbon dioxide or other diluents.

The advantages of this invention will become apparent upon consideration of the following disclosure.

DETAILED DESCRIPTION OF THE INVENTION

One telltale indicator of this invention which is used as a sterilization as well as aeration monitor is prepared in the following manner. A Whatman No. 1 chromatographic filter paper is impregnated with a mixture of the following ingredients in corresponding proportions.

| | |
|---|---|
| Polyethylene Glycol mol. wt. 200 | 40 – 60 gm |
| Polyethylene Glycol mol. wt. 400 | 40 – 60 gm |
| 4(p-nitrobenzyl) pyridine | 1 – 2.5 gm |
| Thiourea | 1 – 1.5 gm |
| Water | 2 – 3 gm |

After coating the paper with this mixture, the excess is wiped off and the filter paper is dried. The amount of dried coating retained by the filter paper is approximately in the range of 0.0200–0.1000 grams per square inch of the filter paper. The indicator thus prepared is cut and packaged in an envelope of approximately 1 ⅝ inch to 2 ⅛ inch size. The front and back of the envelope are made out of different material. The front sheet of the envelope is made out of a transparent sheet of material such as polyester, polyethylene or other suitable polymer and the back is made out of a sheet of spun bonded polyolefin marketed by duPont under the trademark "TYVEK", which permits gas penetration, but not liquids. The thickness of envelope material is 1–3 mils. The envelopes were packaged in a black paper wrapper to prevent their exposure to light.

The indicator envelope is placed with the goods inside a pack and the pack is placed inside the sterilizer. A pack is described as a protective covering or a wrapper. It could be made out of muslin cloth, paper, polyethylene or a combination thereof. When the sterilization cycle is complete the indicator changes in color from white to violet (National Bureau of Standard Color 206–207). The sterilized goods are then placed in an aerator. When the sterilized goods are aerating, the indicator changes color from violet to gray (NBS 264–266) and then to a gray green (NBS 154, 155, 156) which insures that goods are safe to use.

However, it was found that coating formula had to be varied in the case of sterilization of PVC goods such as tubing, face masks etc since PVC absorbs high quantities of ethylene oxide gas its rate of sterilization and aeration varied from other goods. The following formula for the coating was found most effective.

| Polyethylene Glycol mol wt. 1500 | 90 to 100 gm |
| --- | --- |
| 4(p-nitrobenzyl) pyridine | 1.5 to 3.5 gm |
| Thiourea | 1 to 1.5 gm |
| Water | 2 to 3 gm |

The indicator using this coating is prepared exactly in the same manner as described above. In the case of PVC at the end of sterilization indicator color changes to violet (NBS 207–208) and then at the end of aeration cycle to gray green (NBS 154, 155, 156).

Though specific embodiments are described many variations can be made in the materials. For instance, the substrate for carrying out the indicator could be a fabric, paper, plastic film, cardboard or any other material capable of carrying it. The envelope material is not limited to TYVEK (Reg. Trademark of duPont) and gas permeable material. Further, polyethylene glycol of various molecular weights have been tried it was found that the molecular weight has to be properly controlled to coordinate the color change with the carrier. Other aliphatic hydroxy compounds monomeric as well as polymeric such as ethanol, isopropanol, butanol, ethylene glycol, and propylene glycol, were tried and worked as well.

Polyethylene glycols of molecular weight 1500 and 200–400 were preferred because:
1. They are not basic.
2. They give an appropriate color change.
3. They are good solvents for 4(p-nitrobenzyl) pyridine
4. They are good carriers.

To control the light sensitivity of 4-(p-nitrobenzyl) pyridine various photo-inhibitors were tried as additives but they interfered with the indicator color or with the ethylene oxide sensitivity. Thiourea was found most suitable. Water is needed in the formula though its purpose cannot be ascertained.

The factors effecting the sterilization process in a sterilizing chamber are the ethylene oxide gas concentration, relative humidity, temperature and time. Variation in any one of these factors will affect the other factors quantitatively to achieve sterilization. Thus, a variation in any one of the abovementioned parameters can influence the rate and/or intensity of the color formation in the indicator.

The formation of color increases in intensity as the concentration of ethylene oxide increases. Also, the formation of color occurs more rapidly as the concentration of ethylene oxide increases.

The formation of color increases in intensity as the relative humidity increases when ethylene oxide is present. Also, the formation of color occurs more rapidly as the relative humidity is raised when ethylene oxide is present.

The formation of color increases in intensity as the temperature is increased when ethylene oxide is present. Also, the formation of color occurs more rapidly as the temperature is increased when ethylene oxide is present.

Because of the known effect of ethylene oxide at various concentrations and temperatures and humidities on microbes when exposed for time intervals, the aforementioned telltale indicator indirectly relates that a sterilizing action is taking place.

The telltale indicator of this invention is designed to indicate these specific color changes when the relative humidity in the sterilizer is controlled to 30–50%. Different color indication will be obtained if the quantities of the ingredients 4(p-nitrobenzyl) pyridine and polyethylene glycol are varied or the molecular weight of the glycol is changed. In order to get a particular color change from white to violet to gray green the composition of the ingredients and their corresponding proportions claimed here have been carefully calculated and selected from many examples run in the laboratory.

Thus, variations in the indicator color changes are possible with the variation of composition and the corresponding proportions or the variation in the thickness of the indicator coating. Other modifications and ramifications of the present invention would appear to those skilled in the art upon a reading of this disclosure. These are intended to be included within the scope of this invention.

We claim:
1. A method of monitoring a sterilization and aeration process employing ethylene oxide as sterilant in presence of controlled humid atmosphere and temperature comprising:
   a. exposing goods and an indicator to the sterilant till the indicator undergoes a color change;
   b. placing the goods and said indicator in an aeration chamber till the indicator undergoes another color change.
2. Method of claim 1 wherein the step (a) the indicator shows a color change from white to violet.
3. Method of claim 1 wherein in the step (b) the indicator shows a color change from violet to gray green.
4. Method of claim 1 where the indicator comprises:
   a. carrier means;
   b. an indicator composition carried by the carrier means.
5. Method of claim 4 where carrier means is Whatman No. 1 filter paper.
6. Method of claim 4 wherein the indicating composition changes color from white to violet upon sterilization and from violet to gray green upon aeration.
7. Method of claim 4 where quantity impregnated upon carrier means is approximately 0.0200–0.1000 gms per square inch.
8. Method of claim 4 wherein the carrier means is enclosed in an enclosure.
9. Method of claim 8 wherein the enclosure is an envelope.
10. Method of claim 4 wherein the indicating composition comprises the following ingredients
    4(p-nitrobenzyl) pyridine
    Polyethylene Glycol
    Thiourea
    Water
11. Method of claim 10 where the proportions of the ingredients are:

| Polyethylene Glycol Mol wt. 200 | 40 – 60 gms |
| --- | --- |
| Polyethylene Glycol Mol wt. 400 | 40 – 60 |
| 4(p-nitrobenzyl) pyridine | 1 – 2.5 |
| Thiourea | 1 – 1.5 |
| Water | 2 – 3 |

12. Method of claim 10 where the proportions of the ingredients are:

| | |
|---|---|
| Polyethylene Glycol mol. wt. 1500 | 90 – 100 gms. |
| 4(p-nitrobenzyl) pyridine | 1.5 – 3.5 |
| Thiourea | 1 – 1.5 |
| Water | 2 – 3 |

13. A composition of mixture comprising the following in corresponding proportions:

| | |
|---|---|
| Polyethylene Glycol mol. wt. 200 | 40 – 60 gms |
| Polyethylene Glycol mol. wt. 400 | 40 – 60 |
| 4(p-nitrobenzyl) pyridine | 1 – 2.5 |
| Thiourea | 1 – 1.5 |
| Water | 2 – 3 |

14. A composition of mixture comprising the following in the corresponding proportions:

| | |
|---|---|
| Polyethylene Glycol mol. wt. 1500 | 90 – 100 gms |
| 4(p-nitrobenzyl) pyridine | 1.5 – 3.5 |
| Thiourea | 1 – 1.5 |
| Water | 2 – 3 |

* * * * *